United States Patent [19]

Christenson et al.

[11] Patent Number: 5,137,579
[45] Date of Patent: Aug. 11, 1992

[54] MENTHYL PYRAN AND SMOKING COMPOSITIONS COMPOUNDS

[75] Inventors: Philip Christenson, Midland Park, N.J.; Robert Eilerman, Merrick, N.Y.

[73] Assignee: BASF K&F Corporation, Whippany, N.J.

[21] Appl. No.: 331,906

[22] Filed: Mar. 31, 1989

[51] Int. Cl.$^5$ .................. A24B 3/12; C07D 31/14
[52] U.S. Cl. ....................... 131/277; 549/397
[58] Field of Search ............ 131/277, 276, 278; 549/399

[56] References Cited

U.S. PATENT DOCUMENTS

| | | |
|---|---|---|
| 3,312,226 | 4/1967 | Bavley et al. |
| 3,332,428 | 7/1967 | Mold et al. |
| 4,212,310 | 7/1980 | Van Auken et al. |
| 4,366,317 | 12/1982 | Haut et al. |
| 4,532,944 | 8/1985 | Podraza |
| 4,540,004 | 9/1985 | Podraza et al. |
| 4,578,486 | 3/1986 | Podraza |

OTHER PUBLICATIONS

Sakata, I. et al. "Synthesis & Properties of Methyl Glycosides" Agic. Biol. Chem. 43(2) 307–312 (1979).

Chem Ab. 88-0244/11/04 Hasegawa KK.
Stahl-Biskup, E. "Monoterpene Glycosides, State of the Art" Flavor & Frag. J., vol. 2, pp. 75–82 (1987).

Primary Examiner—V. Millin
Attorney, Agent, or Firm—Kenyon & Kenyon

[57] ABSTRACT

Menthyl pyran compounds are provided repesented by the formula 1:

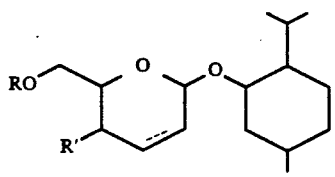

wherein R is H or lower acyl or 1–3 carbon atoms; R' is H, hydroxyl, or $C_{1-3}$ acyloxy, and the dotted line represents an optional double bond.

Use of the compounds provides a menthol note upon pyrolysis or hydrolysis. Smoking compositions containing a compound of formula 1 are also included.

21 Claims, No Drawings

MENTHYL PYRAN AND SMOKING COMPOSITIONS COMPOUNDS

FIELD OF THE INVENTION

This invention relates to novel menthyl pyran compounds which are useful in consumable products, such as those containing tobacco or a tobacco subsitute. The invention also provides a process for preparing these compounds as well as smoking compositions which incorporate the compounds of the invention in natural or non-tobacco substitutes.

BACKGROUND OF THE INVENTION

Menthols, because of their desirable minty flavor and pleasant cooling effect, have been widely used as flavor additives for a variety of consumer products such as tobacco products, gums, medicinal products, toothpaste, foodstuffs, creams and lotions. Menthol is a particular aglycone which be derived from monoterpene glycosides, found in essential oil-containing plants. Such monoterpene glycosides function in the biosynthesis of terpenes as reactants or in the accumulation of essential oils as transport derivatives of free monoterpenes. Many glycosides of monoterpene alcohols are found in nature. See E. Stahl-Bishop, "Monoterpene Glycosides, State-of-the-Art", *Flavor and Fragrance Journal*, 2:75-82 (1987). The isolation and synthesis of menthols with the aim of developing menthol derivatives having good solubility in water has been described in I. Sakata and H. Iwamura, "Synthesis and Properties of Menthyl Glycosides", *Agric. Biol. Chem.*, 43:307-312 (1979). These menthyl glycosides were determined to release menthol upon pyrolysis or hydrolysis.

Menthol is extensively used in tobacco products because of the refreshing cooling effect it imparts to tobacco smoke. Unfortunately, the high degree of volatility and ease of sublimation of menthol have presented problems in various manufacturing operations, such as packaging and handling, and in addition have resulted in a decreased shelf-life of the menthol-containing product due to losses of menthol by diffusion during storage. This problem is especially acute for menthol flavored filter cigarettes. During the processing and storage of this type of product, volatile menthol flavorants migrate from the tobacco and are irreversibly bound by the active adsorbents in the filter or the packaging. The menthol flavorant is therefore depleted and the effectiveness of the active adsorbent in the filter in selectively removing undesirable smoke components may be altered as well.

There has accordingly been considerable research aimed at developing methods of containing and preserving the menthol until it is used. Attempts to adsorb menthol on a support, such as charcoal or diatomaceous earth, and then adding the resultant composition to the tobacco have not been satisfactory. The menthol yields from such adsorbents are typically very low. Furthermore, this technique necessarily involves the incorporation of the adsorbent into the tobacco. The presence of the adsorbent in the tobacco often gives an undesirable appearance to the tobacco and may result in uneven burning of the tobacco. Efforts to contain menthol by microencapsulation in polymeric materials have also been largely unsuccessful.

In order to overcome these difficulties, research in this area has for many years been directed at preparing menthol derivatives which release menthol upon pyrolysis or hydrolysis. Various ester and carbonate derivatives of menthol which function in this manner are known.

For example, U.S. Pat. No. 3,312,226 reports that the ester compound 1-menthyl linalool carbonate, upon addition to smoking tobacco compositions, releases menthol during smoking due to the pyrolysis of the carbonate ester. However, such simple carbonate esters are not entirely satisfactory. Like menthol, they tend to migrate in the tobacco and accordingly hinder the quantitative release of menthol to the tobacco during smoking. Moreover, the second alcohol of the carbonate ester may be chemically altered during pyrolysis, resulting in the production of undesirable chemical fragments which impart a chemical aftertaste to the product.

U.S. Pat. No. 3,332,428 and U.S. Pat. No. 3,419,543 also utilize a carbonate ester to bind the menthol to a releasing agent. The smoking tobacco compositions of these patents, however, contain a menthyl carbonate ester of a polyhydroxy compound, such as a monosaccharide, disaccharide, trisaccharide, or glycol, which under smoking conditions, decomposes to release free menthol into the mainstream smoke. However, because these saccharides and glycols have only primary or secondary alcohol linkages, free menthol is produced upon pyrolysis with only limited efficiency.

U.S. Pat. Nos. 4,119,106, 4,092,988, 4,171,702, 4,177,339, and 4,212,310 describe the attaching of the menthyl carbonate ester derivative to other oligomeric and polymeric materials. Compositions containing these materials release volatile flavorants, including menthol, upon pyrolysis which occurs during the smoking of the tobacco compositions.

U.S. Pat. Nos. 4,532,944 and 4,578,486 describe smoking compositions which contain dicarbonate este compounds as flavoring additives. These compounds pyrolyze into menthol and other products which enhance the flavor of the mainstream smoke and the aroma of sidestream smoke.

U S. Pat. No. 4,540,004 discloses smoking compositions containing a 1,4-dioxane tetracarbonate derivitive. Under smoking conditions, this flavorant-release composition imparts an improved flavor to mainstream smoke and an improved aroma to sidestream smoke.

Japanese Pat. No. 2,283,992-A discloses certain glycosyl mono-menthyl orthoacetates which decompose in the presence of water or acid to liberate menthol. These compounds may be used as components for food and drinks.

The compounds and compositions disclosed in each of the references may yield a relatively small amount of available menthol, demonstrate a low level of stability, release other unwanted materials along with menthol, and cause difficulties in the preparation.

It is therefore an object of the present invention to develop compounds which release menthol upon pyrolysis or hydrolysis.

Another object of the invention is to provide a process for the preparation of the compounds of the present invention.

It is yet another object of this invention to provide a smoking composition which contains an effective amount of the compounds of the present invention in combination with tobacco or a tobacco substitute.

SUMMARY OF THE INVENTION

In accordance with the above-mentioned and other objects, the following invention is directed to novel menthyl pyran compounds having the formula:

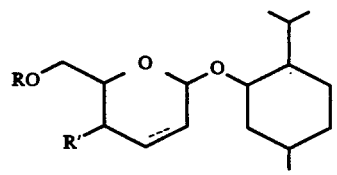

wherein R is hydrogen or lower acyl of 1-3 carbons; R' is hydrogen, a hydroxyl group or an acyloxy group of 1 to 3 carbons, and the dotted line represents an optional double bond.

The invention described herein further encompasses a smoking composition containing tobacco or a tobacco substitute in combination with a compound of formula I, present in an amount effective to impart a menthol aroma to the tobacco or tobacco substitute upon smoking.

DETAILED DESCRIPTION OF THE INVENTION

As used herein the term "acyl" (and the acyl portion of acyloxy) means an organic radical derived from an organic acid by the removal of a hydroxyl group. Lower acyl, unless otherwise defined, means acyl containing 1 to 3 carbon atoms.

The compounds of formula I are effective for imparting a menthol flavor or aroma to the product into which it is incorporated, at w/w concentrations ranging from about 0.0001% to about 5.0%. A preferred concentration range for the compounds of formula I is from about 0.05 to about 1.5 percent. An optimal percentage concentration for the compounds of formula I is 1% by weight.

The novel menthyl pyran compounds described herein possess little or no odor or flavor themselves, but release menthol upon hydrolysis and/or pyrolysis. These compounds may thus be used to flavor a variety of consumer products such as tobacco products, non-tobacco smoking substitutes, medicinal products, toothpaste and certain foodstuffs.

The terms "tobacco" and "tobacco substitutes" are used in the conventional sense, and include smokable as well as non-smokable forms in which tobacco is regularly used, e.g., cigarettes, snuff, chewable compositions, etc.

The menthyl pyran compounds of the present invention are represented by the general formula:

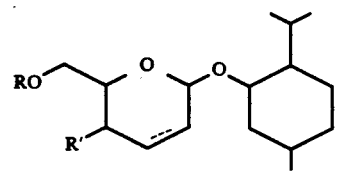

wherein R represents hydrogen or a lower acyl group of 1 to 3 carbon atoms; R' is hydrogen, a hydroxyl group, or an acyloxy group containing 1 to 3 carbons, and the dotted line represents an optional double bond.

A preferred form of the menthyl pyran compounds of the present invention has the following formula:

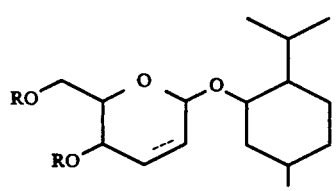

wherein R is hydrogen or lower acyl of 1-3 carbons and the dotted line represents an optional double bond.

Preferred compounds within the scope of formula 1 include those compounds where R represents hydrogen. Those compounds where R represents lower acyl are also useful as intermediates for the preparation of compound 1 wherein R represents hydrogen.

Preferred species falling within the scope of the invention are presented below in Table I.

TABLE I

| COMPOUND STRUCTURE | NAME |
|---|---|
| 3 | menthyl 2,3-dideoxy-hex-2-enopyranoside diacetate (Ac as used herein represents an acetyl group, CH3C(0)-) |
| 4 | menthyl 2,3-dideoxy-hexapyranoside diacetate |
| 5 | menthyl 2,3-dideoxy-hex-2-enopyranoside |
| 6 | menthyl 2,3-dideoxy-hexapyranoside |
| 7 | 6-menthyloxy-tetrahydro-2H-pyran-2-methanol |

TABLE I-continued

| COMPOUND STRUCTURE | NAME |
|---|---|
| 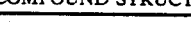 | 6-menthyloxy-tetrahydro-2H-pyran-2-methanol acetate |
| 8 | |

It will recognized by those skilled in the art from teachings herein that the compounds of the invention can exist in several isomeric forms. This invention encompasses all such isomers both in pure form and in mixtures.

The menthyl pyran compounds according to structure 2 may be prepared from the condensation of triacyloxy dihydropyrans with menthol by the following Scheme I.

SCHEME I

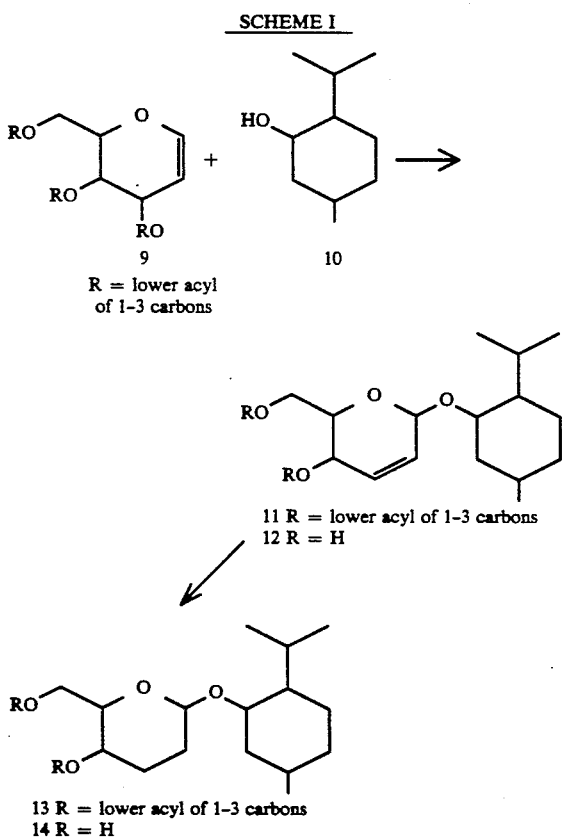

9 R = lower acyl of 1-3 carbons

10

11 R = lower acyl of 1-3 carbons
12 R = H

13 R = lower acyl of 1-3 carbons
14 R = H

According to Scheme I, menthol 10 is condensed with triacyloxydihydropyran 9 in an inert solvent in the presence of an acid catalyst to provide adduct 11. Protic acids such as sulfuric acid, perhcloric acid, p-toluenesulfonic acid or methanesulfonic acid may be used. Lewis acids such as boron trifluoride etherate, zinc chloride, titanium tetachloride, ferric chloride or aluminum chloride may also be used. The preferred Lewis acids include boron trifluoride etherate, zinc choloride or titanium tetrachloride. The most preferred Lewis acid is boron trifluoride etherate.

The reaction may be performed in a variety of inert solvents such as toluene, benzene, xylene, dichloromethane or dichloroethane. Preferred solvents include toluene, benzene or xylene. The most preferred solvent is toluene. The condensation reaction may be performed in a temperature range of from about −10° C. to about 120° C., depending upon the particular Lewis acid and solvent used in the reaction. Where boron trifluoride etherate and toluene are used as the Lewis acid and solvent, the preferred reaction temperature is from about 20° C. to 25° C.

Compound 11 of the invention can be converted to compound 14 by various methods. See, for example, "Survey of Organic Syntheses" by C.A. Buehler and D.E. Pearson, Wiley Interscience, 1970, p. 176. One method which is particularly useful involves the hydrolysis of compound 11 to compound 12 with any of a variety of hydroxides, alkoxides, or carbonates. Group I and Group II metal hydroxides, alkoxides, and carbonates are preferred. Sodium, potassium, lithium and calcium hydroxides or carbonates, sodium, potassium, lithium alkoxides of lower alkanols of 1 to 4 carbon atoms and ammonium hydroxide are more preferred. The most preferred reagents are sodium alkoxides of lower alkanols containing 1 to 4 carbon atoms.

Preferred solvents for use in the hydrolysis reaction include lower alkanols of 1 to 4 carbon atoms, tetrahydrofurans, ethylene glycol, dimethoxyethane, dioxane, water or mixtures of the above. Methanol, ethanol, isopropanol and water or water and alcohol mixtures are the more preferred solvents. The most preferred solvents are methanol and a methanol/water mixture. The hydrolysis reaction may be conducted in the temperature range of about 0° C. to 80° C. The more preferred temperature range is from 0° C. to 50° C. and 10° C. to 35° C. is the most preferred temperature range.

Alternatively, compound 11 may be converted to diol 12 by treatment with a hydride reducing reagent such as lithium aluminum hydride. See, for example, "Reagents for Organic Synthesis Vol. 1" by L.F. Fieser and M. Fieser, Wiley & Sons, Inc., 1967, p. 586.

Diol 12 may then be conveniently reduced to compound 14 with hydrogen in the presence of a catalyst such as platinum, palladium, rhodium, ruthenium or Raney nickel. Platinum or palladium catalysts are preferred. A wide range of solvents may be used in this reaction, among which are ethanol, ethyl acetate, isopropanol, methanol, water and mixtures of the above. Preferred solvents are methanol, ethanol, and isopropanol, with ethanol being the most preferred.

This reduction reaction may be performed at a temperature ranging from about 20° C. to about 100° C. The preferred temperature range is from about 20° C. to about 75° C. and the most preferred temperature range is from 20° C to 40° C.

The hydrogen pressure may range from about 40 psi to about 300 psi, with 50 to 200 psi being preferred. The most preferred pressure range is from 50 to 150 psi.

Compound 11 may be reduced in a similar fashion to provide compound 13 which may then be hydrolyzed to compound 14 in a manner similar to that described above for the conversion of compound 11 to compound 12.

Those preferred menthyl pyran compounds where R' is hydrogen are represented by the following formula 15.

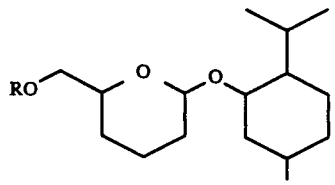

R may be hydrogen or lower acyl containing 1-3 carbons.

The methyl pyran compounds according to compound 15 may be prepared from 3,4-dihydro-2H-pyran-2-carboxaldehyde by either of two routes as described below in Scheme II.

SCHEME II

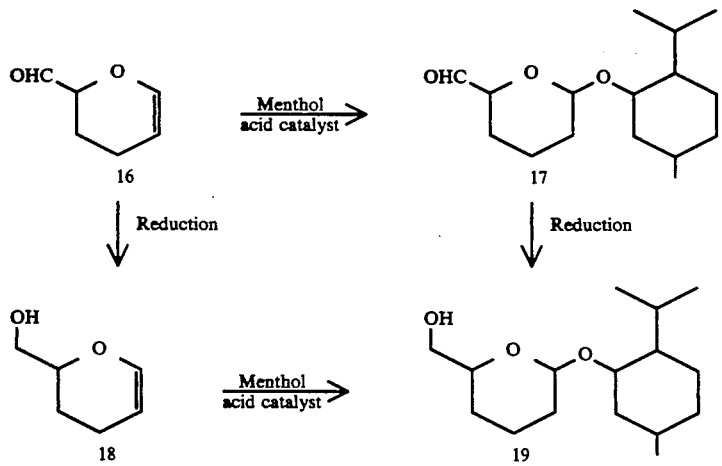

The aldehyde, 3,4-dihydro-2H-pyran-2-carboxaldehyde, compound 16, is a thermal dimer of acrolein and its preparation and reactions are discussed by R. W. Fourie and G. H. Riesser in Chapter 12 of *Acrolein*, C. W. Smith ed., John Wiley & Sons, p. 181-210 (1962).

Menthol may be condensed with compound 16, 3,4-dihydro-2H-pyran-2-carboxaldeyde in the presence of acid to provide compound 17, 6-menthyloxy-tetrahydro-2H-pyran-2-carboxaldehyde. A Lewis acid or a protic acid may be employed, with protic acids being preferred. Aldehyde 17 may be reduced to an alcohol 19, 6-menthyloxy-tetrahydro-2H-pyran-2-methanol, by catalytic hydrogenation for example, over Raney nickel or a nobel metal catalyst. Compound 17 may alternatively be reduced to compound 19 using a hydride reducing agent, such as sodium borohydride or lithium aluminum hydride.

Alternatively, the acrolein dimer 16, can be reduced to an alcohol 18, 3,4-dihydro-2H-pyran-2-menthol, by a variety of methods including sodium borohydride, Meerwein, Ponndorf and Verley reductions and hydrogenation over copper chromite. Addition of menthol to compound 18 in the presence of an acid catalyst provides compound 19.

The following examples are given to illustrate certain preferred embodiments of the invention. It is understood that these examples are illustrative only, and the scope of invention is not be limited thereto.

All parts, proportions, percentages, and ratios used herein are by weight unless otherwise indicated.

EXAMPLE 1

MENTHYL 2,3-DIDEOXY-D-ERYTHRO-HEX-2-ENOPYRANOSIDE

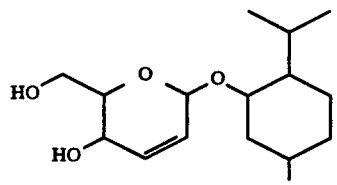

To a cold (19° C.) mixture of triacetyl glucal (105 g, 0.386 mol), l-menthol (75.27 g, 0.482 mol) and toluene (470 mL). was added boron trifluoride etherate (21.92 g, 0.154 mol) over a 10 min. period. The reaction mixture was stirred at 19°-21° C. for 30 min. The mixture was then poured onto a 105 sodium carbonate solution (150 mL). The layers were separated and the aqueous layer was extracted with toluene (2×50 mL). The organic layer was washed with 10% sodium carbonate solution until neutral. After washing with brine, the organic layer was dried over sodium sulfate and the solvent removed to provide crude diacetate. A sample of the crude product was retained for purification (See Example 2).

A mixture of the crude product from above, methanol (500 mL) and sodium methoxide (5.0 g) was stirred at 20°-25° C. for 4 h. After removal of most of the methanol under reduced pressure, the concentrate (about 300 mL) was added to ethyl acetate (400 mL) and water (100 mL). The layers were separated and the aqueous layer was extracted with ethyl acetate (3×100 mL). The combined extracts were washed with brine (33×50 mL) and dried over sodium sulfate. Evaporation of solvent and crystallization of the residue from ethyl acetate and ethanol provided in two crops 67.51 g, (61.6% yield) of menthyl 2,3-dideoxy-D-erthro-hex-2-enopyranoside, mp 153°-154° C., $[\alpha]_D 9.52°$(c, 2.144, ethanol). $^1$H-NMR (250 MHz, CD$_3$OD). $\zeta$0.81 (3H, d, J=6.1 Hz), 0.92 (6H, 2d, J=6.5 Hz), 0.9-2.4 (9H,m), 3.46 (1H, dt, J=3.9 and 10.6 Hz), 3.65-4.82 (3H, m), 4.02-4.13 (1H,m), 5.06 (1H, broad s), 5.7-6.0 (2H, m); $^3$C-NMR (CD$_3$OD)$\zeta$16.82, 21.50, 22.62, 24.71, 27.02, 33.01, 35.66, 44.74, 50.45, 62.92, 64.49, 73.32, 81.67, 97.22, 127.06, 134.47. IR (KBr) $v_{max}$ 3330, 2960, 2930, 1460, 1385, 1370 cm$^{-1}$. MS m/e 253, 235, 224, 129, 111, 86, 55.

EXAMPLE 2

MENTHYL 2,3-DIDEOXY-D-ERYTHRO-HEX-2-ENOPYRANOSIDE DIACETATE

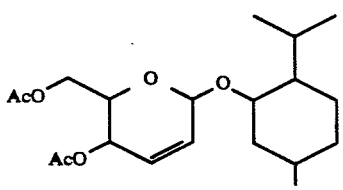

A sample (2g) of the crude diacetate from Example 1 was heated at 50° C. under vacuum (5 mm) to remove most of the menthol. The residue was chromatographed on silica gel 60 (100g) using hexane/ethyl acetate (9:1, then 4:1) as eluant. Solvent was removed from the main fraction to provide 0.61g of menthyl 2,3-dideoxy-D-erythro-hex-2-enopyranoside diacetate as a colorless oil $^1$H-NMR (250 MHz, CDCl$_3$) $\zeta$0.79 (3H, d, J=7.2 Hz), 0.92 (6H, d, J=6.8 Hz), 0.80–2.30 (9H, m), 2.08 (3H, s), 2.12 (3H, s), 3.43 (1H, dt, J =4.1 and 10.5 Hz), 4.13–4.28 (3H, m), 5.11 (1H, s), 5.28 (1H, d, J =7.2 Hz), 5.87 (2H, s). $^{13}$C-NMR $\zeta$16.41, 20.67, 20.82, 21.08, 22.32, 23.61, 25.95, 31.85, 34.53, 43.50, 49.06, 63.51, 65.73, 67.11, 81.26, 96.20, 128.26, 128.57, 170.05, 170.47. IR (film) $v_{max}$2940, 2900, 1740, 1450, 1365cm$^{-1}$. MS m/e 266, 213, 153, 111, 43.

EXAMPLE 3

MENTHYL 2,3-DIDEOXY-D-ERYTHROHEXAPYRANOSIDE

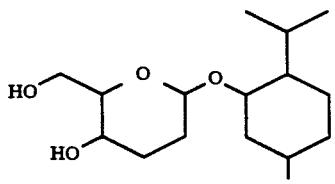

A mixture of menthyl 2,3-dideoxy-D-erythro-hex-2-enopyranoside (60.0g, 0.211 mol), ethanol (850 mL), sodium nitrite (0.020g) and platinum oxide (0.388g) was stirred at 25° C. under a hydrogen atmosphere (150 psi) for 18h. The mixture was filtered and the solvent evaporated in vacuo. The residue was crystallized from ethyl acetate to provide in four crops 51.1 g (85% yield) of menthyl 2,3-dideoxy-D-erythrohexapyranoside mp 99°–100° C., [α]$_D$49.26° (c, 2.45, ethanol). $^1$H-NMR (250 MHz, CDCL$_3$)$\zeta$0.77 (3H, d, J =6.4 Hz), 0.90, (6H, d, J =6.5 Hz), 0.95–2.1 (13H, m), 2.55 (1H, broad s), 2.80 (1H, broad s), 3.32 (1H, dt, J =3.9 and 10.6 Hz), 3.58–3.95 (4H, m), 4.84 (1H, d, J =2.8 Hz). $^{13}$C-NMR (CDCl$_3$)$\zeta$16.46, 21.06, 22.29, 23.66, 26.02, 27.53, 29.93, 31.84, 34.55, 43.30, 49.02, 63.42, 67.74, 73.22, 80.54, 98.28. IR (KBr) $v_{max}$ 3280, 2940, 2920, 1450, 1380, 1355 cm$^{-1}$. MS m/e 286, 252, 226, 131, 113.

EXAMPLE 4

PREPARATION OF A FILTER CIGARETTE CONTAINING THE COMPOUND OF EXAMPLE 1

A standard brand American filter cigarette was injected with 75 uL of a 10% solution of menthyl 2,d-dideoxy-D-erythro-hex-2-enopyranoside. Upon smoking the treated cigarette, the smoker experienced the typical cooling effect of menthol along with a slight fermented-type note. The impact was judged to be greater than 25% of the impact expected if the cigarette had contained an equivalent weight of l-menthol.

EXAMPLE 5

PREPARATION OF A FILTER CIGARETTE CONTAINING THE COMPOUND OF EXAMPLE 2

A standard brand American filter cigarette was injected with 15 uL of a 50% solution of menthyl 2,3-dideoxy-D-erythrohexapyranoside. Upon smoking the treated cigarette, the smoker strongly experienced the typical cooling effect of menthol. No additional by-notes were observed. The impact was judged to be 50–60% of the impact expected if the cigarette had contained an equivalent weight of l-menthol.

While certain preferred embodiments have been described herein in detail, numerous alternative embodiments are contemplated as falling within the spirit of the invention. Consequently, the scope of the appended claims is not to be limited thereby.

We claim:

1. A compound represented by formula 1:

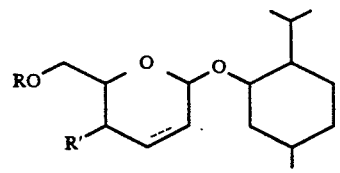

wherein R is hydrogen or a lower alkyl group containing 1 to 3 carbon atoms; R' is hydrogen, a hydroxyl group or an acyloxy group containing 1 to 3 carbons atoms, and the dotted line represents an optional double bond.

2. The compound according to claim 1 wherein the optional double bond represented by the dotted line is absent.

3. The compound according to claim 2 wherein R' is hydrogen.

4. The compound according to claim 3 wherein R is hydrogen.

5. The compound according to claim 3 wherein R is a lower acyl group containing 1 to 3 carbons.

6. The compound according to claim 2 wherein R represents hydrogen and R' represents hydroxyl.

7. The compound according to claim 2 wherein R represents a lower acyl group containing 1 to 3 carbon atoms and R' represents a lower acyloxy containing 1 to 3 carbons.

8. The compound according to claim 1 wherein the optional double bond represented by the dotted line is present.

9. The compound according to claim 8 wherein R is hydrogen and R' is a hydroxyl group.

10. The compound according to claim 8 wherein R is a lower acyl group containing 1 to 3 carbon atoms and R' is a lower acyloxy group containing 1 to 3 carbon atoms.

11. A compound having the name:
menthyl 2,3-dideoxy-hex-2-enopyranoside diacetate;
menthyl 2,3-dideoxy-hexapyranoside diacetate;
menthyl 2,3-dideoxy-hex-2-enopyranoside;
menthyl 2,3-dideoxy-hexapyranoside;
6menthyloxy-tetrahydro-2H-pyran-2-methanol, or
6-menthyloxy-tetrahydro-2H-pyran-2-methanol acetate.

12. A smoking composition which comprises tobacco or a tobacco substitute in combination with a compound of formula I:

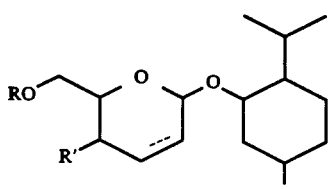

wherein R is hydrogen or $C_{1-3}$ lower acyl;
R' is H, hydroxyl or $C_{1-3}$ acyloxy, and
the dotted line is an optional double bond,
said compound being present in an amount effective for imparting a menthol aroma to the tobacco or tobacco substitute upon pyrolysis.

13. The smoking composition according to claim 12 wherein the concentration of said compound is from about 0.0001% to about 5.0% by weight.

14. A smoking composition according to claim 13 wherein the concentration of said compound is from about 0.05 to about 1.55 by weight.

15. A smoking composition according to claim 14 wherein the concentration of said compound is 1.0% by weight.

16. A smoking composition in accordance with claim 12 wherein R represents H and R' represents hydroxyl.

17. A smoking composition according to claim 16 wherein the concentration of said compound ranges from about 0.0001% to about 5.0% by weight.

18. The smoking composition according to claim 17 wherein the concentration of said compound is 1.0% by weight.

19. The smoking composition according to claim 16 wherein the concentration of said compound ranges from about 0.05% to about 1.5% by weight.

20. A composition suitable for human consumption which comprises a consumable material in combination with an effective amount of a compound of the formula:

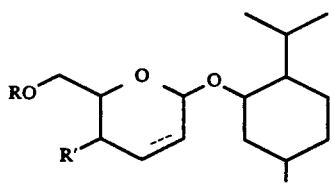

wherein R is H or $C_{1-3}$ lower acyl;
R' is H, hydroxyl or $C_{1-3}$ lower acyloxy, and the dotted line is an optional double bond.

21. The compositoin according to claim 20, wherein said consumable material is a foodstuff.

* * * * *